US00PP28613P2

(12) United States Plant Patent
Hansen

(10) Patent No.: US PP28,613 P2
(45) Date of Patent: Nov. 7, 2017

(54) X MANGAVE PLANT NAMED 'PINEAPPLE EXPRESS'

(50) Latin Name: ***Manfreda×Agave* hybrid**
Varietal Denomination: Pineapple Express

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 81 days.

(21) Appl. No.: 14/999,084

(22) Filed: Mar. 29, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden

(57) ABSTRACT

A new and unique X Mangave plant named 'Pineapple Express' characterized by rapid growth rate and compact habit of stiff, upright to outward pointing, succulent foliage gray-green coloring and burgundy speckling. The green flowers on heavily-branched, tall, stiff, purplish tinted scapes are loaded with nectar are highly attractive to hummingbirds.

1 Drawing Sheet

Botanical classification: *Manfreda×Agave* hybrid.
Variety denomination: 'Pineapple Express'.

BACKGROUND OF THE INVENTION

The present invention relates to the new and distinct X Mangave plant, X Mangave 'Pineapple Express' hybridized by the inventor at a wholesale perennial nursery in Zeeland, Mich., USA as an individual select seedling from a cross between X Mangave 'Jaguar' (not patented) times X Mangave 'Bloodspot' (not patented). The cross was performed on Jul 12, 2011 and seeds harvested on Nov. 7, 2011. Through repeated trials beginning in 2012 at the same nursery and since the new plant was referred to by the breeder code XMAN11-18-05. The new plant has been successfully asexually propagated initially by division at the same nursery in Zeeland, Mich. and also by tissue culture. Both methods of asexual propagation systems have been found to produce stable and identical plants that maintain all the unique characteristics of the original plant.

No plants of X Mangave 'Pineapple Express' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

X Mangave 'Pineapple Express' differs from its parents as well as all other *Manfreda, Agave* and X Mangave known to the applicant. Compared to the female parent, X Mangave 'Jaguar', the new plant is smaller, more compact, and the foliage is shorter. Compared to the male parent, 'Bloodspot', the new plant is less compact, has less stiffer foliage with an abundance of greyed-purple speckling. The most similar known X Mangave cultivar is 'King Cobra' (co-pending U.S. Plant Patent Application). Compared to 'King Cobra', 'Pineapple Express' has foliage that is more upright, less broad, with larger burgundy speckling and less glossiness to the adaxial and abaxial leaf surfaces.

The new plant, 'Pineapple Express', is unique from all of these *Agave, Manfreda* and X Mangave known to the inventor by the following combined traits:

1. Stiff, upright to outward pointing, succulent foliage with compact habit;
2. Gray-green leaves with large speckling of burgundy spots;
3. Moderate to rapid growth rate with good natural pup production;
4. Flowers on stiff, tall, lightly-branched scapes with purplish tinting.

BRIEF DESCRIPTION OF THE DRAWINGS

The photograph of the new plant demonstrates the overall appearance of the new plant including the unique traits as a two-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
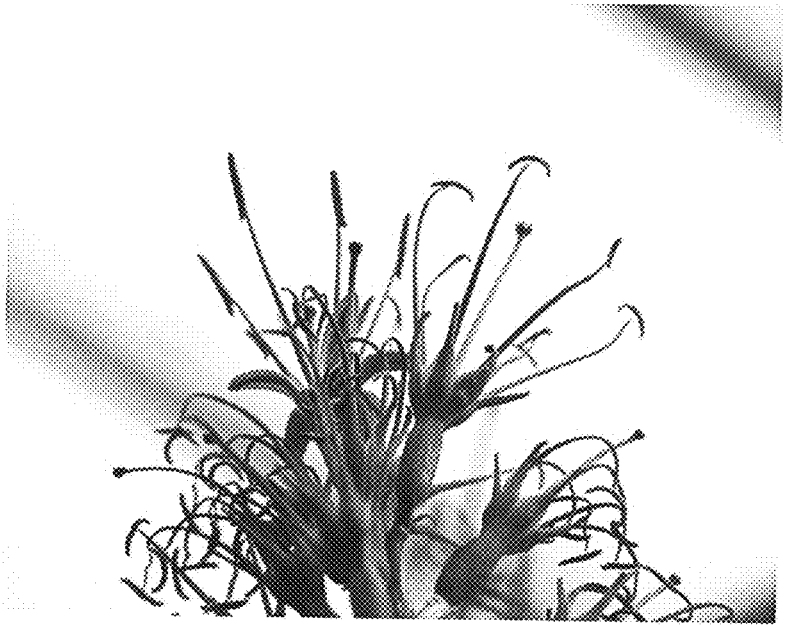
FIG. 1 shows a close-up of flowers of the new plant.
Figure 2:
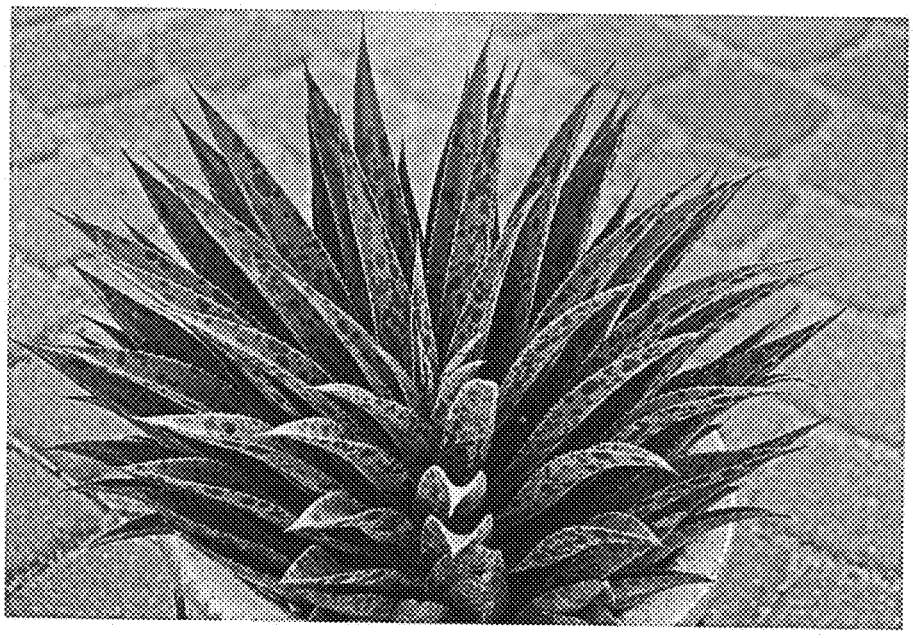
FIG. 2 shows the compact foliage of the new plant in a container.

The following descriptions and color references are based on the 2001 edition of The Royal Horticultural Society Colour Chart except where common dictionary terms are used. The new plant, X Mangave 'Pineapple Express', has not been observed under all possible environments. The phenotype may vary slightly with different environmental conditions, such as temperature, light, fertility, moisture and maturity levels, but without any change in the genotype. The following observations and size descriptions are of a two-year-old plant in a commercial wholesale greenhouse in Zeeland, Mich. with supplemental water and fertilizer as needed.

Botanical classification: X Mangave hybrid.

Variety denomination: 'Pineapple Express'.

Parentage: Female or seed parent X Mangave 'Jaguar'; male or pollen parent X Mangave 'Bloodspot'.

Propagation: Division and sterile plant tissue culture.

Time to initiate roots from tissue culture: About 18 days.

Growth rate: Rapid.

Crop time: About 10 to 14 weeks to finish during lengthening spring days from an established 25 mm tissue culture plug to a finished 65 mm diameter container.

Rooting habit: Fleshy, lightly branching, with roots up to 15 cm long.

Root color: Nearest RHS 158C.

Plant shape and habit: Succulent herbaceous polycarpic perennial with basal rosettes of about 75 fleshy leaves radially emerging from central rhizome, producing a symmetrical rounded mound.

Plant size: Foliage height about 20.0 cm tall from soil line to the top of the leaves and about 45.0 cm wide at the widest point at soil line.

Foliage description: Gladiate; simple, fleshy, glabrous; glaucous; margins finely dentate with flexible teeth; apex acute with mucro; base truncate, sessile, clasping.

Number of leaves: About 50 per plant.

Leaf blades: Finely dentate; to about 29.0 cm long, about 3.5 cm wide at base and 5.0 mm thick, average about 28.0 cm long, 3.0 cm wide and 4.0 mm thick; usually bi-laterally symmetrical; glabrous and glaucous above and below; with irregular speckles intensified with higher ultra violet light of between about 1.0 diameter to about 6.0 mm across and about 12.0 mm long.

Foliage fragrance: None observed.

Leaf blade color:

*Adaxial* (*young*).—Nearest RHS 138D with irregular speckles nearest RHS 138A and leaf edge and dentation frequently developing tinting of nearest RHS 187B.

*Abaxial* (*young*).—With heavy glaucous covering lighter than RHS N138D with speckles nearest RHS 147A with slight tinting of nearest RHS N187C.

*Adaxial* (*mature*).—Lighter than either RHS 147D and RHS 148D with speckles of between RHS N187A and RHS N187B and slight purplish tinting toward distal one third of nearest RHS N186C.

*Abaxial* (*mature*) *center*.—Nearest RHS 137A with speckles absent in lowest leaves or between RHS N187A and RHS N187B.

Mucro: Flexible; straight, about 5.0 mm long.

Mucro color: Between RHS 166A and RHS 183A.

Spine texture: Flexible, glabrous, sharply-pointed.

Petiole: Sessile.

Veins: Parallel; not distinct.

Peduncle: Terete; glaucous; glabrous; stiff; strong; with about 30 cauline leaves erect to nearly adpressed along surface; about 265 cm long and 2.1 cm diameter at base; attitude upward, erect.

Peduncle color: Blend between RHS N187C and RHS 182C; highly branched.

Peduncle branches: Terete; glaucous; glabrous; at about 45 degree angle from main peduncle; about 32 per scape; lowest branches with about 12 flowers, distal branches containing 2 flowers; to about 18.0 cm long and 7.0 mm diameter at base, decreasing distally.

Pedicel: Terete; glaucous; glabrous; stiff; strong; about 7.0 mm long and 3.5 mm diameter.

Pedicel color: Between RHS N138A and RHS 137A.

Cauline leaves: Gladiate; simple, fleshy, glabrous; glaucous; margins finely dentate with flexible teeth; apex acute with mucro; base truncate, sessile, clasping; about 15.0 cm long and 3.8 around base, decreasing distally.

Cauline leaf color: Abaxial nearest RHS 138C with base nearest RHS 183C, tinting throughout of nearest RHS 183C and speckles of between RHS 183B and RHS 183C; adaxial nearest RHS 146D with speckles of nearest RHS 182B.

Buds one day prior to opening: Elongated globose; glabrous, glaucous; terminal bulb about 2.3 cm long and about 1.0 cm across; proximal tube about 2.0 cm long and 6.0 mm across; overall about 4.3 cm long.

Bud color: Nearest RHS N138A.

Flower description: Perfect, actinomorphic; about 7.5 cm long and opening to about 3.7 cm across at outside of anthers; lasting about 3 to 4 days per flower; flowering period about four weeks in late winter in Michigan greenhouse; producing abundant nectar; approximately 220 flowers per scape; attitude upwards.

Flower fragrance: Faintly sweet.

Tepals: Six; glaucous abaxial; glabrous both adaxial and abaxial; acute apex and fused base; in two sets of three; outer set about 2.4 cm long and about 3.3 mm wide at base; inner set about 2.4 cm long and 3.3 mm wide at base; inner set creased along edge where overlapped with outer set while in bud.

Tepal color: Outer set adaxial and abaxial nearest RHS 146D, inner set adaxial and abaxial nearest RHS 146D and creased margin nearest RHS 145A abaxial and adaxial.

Androecium: Six.

*Filaments*.—Six; stiff and straight; about 7.0 cm long and 2.0 mm diameter at base; color nearest RHS 160D with dense speckling of nearest RHS 183A.

*Anther*.—Dorsifixed; longitudinal; about 1.9 cm long and 2.0 mm diameter before dehiscing; after dehiscence curving backward; color nearest RHS 177B with speckles of between RHS 151D and RHS 153D.

*Pollen*.—Abundant; color nearest RHS 2A.

Gynoecium: Single.

*Style*.—5.1 cm long and 1.7 mm diameter at base; color blend nearest RHS 160C with dense speckling of RHS 183A.

*Stigma*.—Globose, apex tri-lobed; about 3.0 mm tall and 3.0 mm across top; color side and top nearest RHS 187B; top stigmatic surface in tri-pointed star with color nearest RHS 156D.

*Ovary*.—Inferior.

Fruit: Dehiscent, tri-valved, loculicidal capsule; apex abruptly acute; base slightly tapered; about 3.0 cm long and 1.5 cm across.

Fruit color: When immature nearest RHS N146D; at dehiscence blend between RHS 199C and RHS 161B.

Seed: Flattened, near round; about 4.0 mm across and about 1.0 mm thick; color nearest RHS 202A.

Disease resistance: X Mangave 'Pineapple Express' has not been observed to be resistant to diseases common to other X Mangave beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X Mangave plant named 'Pineapple Express' as herein described and illustrated, suitable as a potted plant or for the garden.

* * * * *